United States Patent
Chichereau et al.

(10) Patent No.: US 6,556,655 B1
(45) Date of Patent: Apr. 29, 2003

(54) METHOD FOR AUTOMATIC DETECTION OF GLANDULAR TISSUE

(75) Inventors: Claire Chichereau, Paris (FR); Jean Bossaert, Albis (FR)

(73) Assignee: GE Medical Systems SA, Buc (FR)

( * ) Notice: Subject to any disclaimer, the term of this patent is extended or adjusted under 35 U.S.C. 154(b) by 0 days.

(21) Appl. No.: 09/450,918

(22) Filed: Nov. 29, 1999

(51) Int. Cl.[7] .................................................. A61B 6/00
(52) U.S. Cl. ............................ 378/108; 378/37; 378/62
(58) Field of Search ........................... 378/37, 62, 108

(56) References Cited

U.S. PATENT DOCUMENTS

| | | | |
|---|---|---|---|
| 5,526,394 A | | 6/1996 | Siczek et al. ................. 378/37 |
| 6,005,911 A | * | 12/1999 | Cheung ........................ 378/37 |
| 6,035,056 A | * | 3/2000 | Karssemeijer .............. 382/132 |
| 6,084,940 A | * | 7/2000 | Van Asten ................. 378/98.7 |
| 6,028,710 A1 | * | 3/2001 | Nagai .......................... 378/108 |

FOREIGN PATENT DOCUMENTS

| | | |
|---|---|---|
| DE | 3641992 | 6/1988 |
| EP | 0777406 | 4/1997 |

\* cited by examiner

*Primary Examiner*—Robert H. Kim
*Assistant Examiner*—Allen C. Ho
(74) *Attorney, Agent, or Firm*—Jay L. Chaskin

(57) ABSTRACT

The method consists of subjecting the organ to pre-exposure with a low dose of rays, creating in the field of the pre-exposure image a multi-cellular image in which each cell represents the mean signal level of a predetermined number of pixels of the detector, selecting from the columns the cell of minimum signal level most distant from a reference point, establishing about this cell a band parallel to the reference point and selecting from the band the cell having the absolute minimum signal level. The parameters of exposure may then be set from this absolute minimum

8 Claims, 3 Drawing Sheets

METHOD FOR AUTOMATIC DETECTION OF GLANDULAR TISSUE

BACKGROUND OF THE INVENTION

The present invention relates to the field of radiologic imaging, which makes it possible to visualize an organ or organ part, usually of the human body.

In digital radiology, the digital image obtained depends, among other things, upon the dose of X-rays and the nature of the tissue of the organ examined. The organ examined may consist of tissues of various natures and the zone of interest of the organ examined may consist of a tissue of a given nature. This is the case in particular of the breasts, which are made up of adipose tissues and of glandular tissues.

On present-day mammography apparatus, an automatic exposure (AEC) cell is positioned behind what is presumed to be the glandular tissue. This positioning is done blindly.

BRIEF SUMMARY OF THE INVENTION

It would thus be desirable to be able to automatically detect a tissue of determined nature, such as the glandular tissue of the breast and other tissues of the organ examined, in order to set the parameters of exposure as a function of the nature of the tissue to be examined.

The subject of the present invention thus is a method of automatic detection of a tissue of predetermined nature in an organ part examined by digital x-ray radiography and the use of said detection to establish the parameters of exposure of the organ part.

An embodiment of the method comprises the steps of:

a) establishing parameters of pre-exposure from a table of automatic optimization of parameters, a given theoretical composition and an estimated radiologic thickness of the organ part examined and for a low but sufficient dose of X-rays to obtain a pre-exposure image of sufficient quality for the differentiation of tissues of the organ part examined;

b) establishing a minimum dose level and of a maximum dose level from a predetermined mechanical thickness of the organ part examined and conversion of these dose levels into a minimum threshold signal level and a maximum signal threshold level, readable by a detector;

c) pre-exposing the organ part examined to obtain a pre-exposure image;

d) creation in a zone of interest of the field of the pre-exposure image of a multi-cellular image comprising columns in which each cell indexed with regard to a reference point represents the logarithmic mean of the signal levels between the minimum threshold level and the maximum threshold level of a predetermined number of pixels of the detector;

e) determination in each column of the position, with respect to the reference point, of the cell having the minimum signal level to obtain a set of retained cells;

f) selection from the set of retained cells of the one whose position is most distant from the reference point;

g) determination of a band, parallel to the reference point, including the retained cell, the width of which is proportional to the distance of the cell selected with respect to the reference point and search in this band for the cell having an absolute minimum signal level; and h) using the absolute minimum signal level to establish the parameters of exposure of the organ part examined by X-rays.

The organ part examined is compressed by means of a compression device, such as a compression pad in the case of a breast, and it is preferable to ensure that this device is not located in the field of the image, or if it is there, to modify the mode of detection of the zone of interest.

To do this, after step (d), the following steps are taken:

(1) elimination of all cells not including enough pixels of a value between the minimum threshold level and the maximum threshold level;

(2) establishing a minimum position and a maximum position in depth, determined from the reference point, of a device which may perhaps be present for compression of the organ part examined;

(3) establishing a threshold value;

(4) establishing a line situated between the minimum and maximum positions in depth of any possible compression device and parallel to the reference point;

(5) comparing the threshold value of the variation in signal level between two consecutive cells along the line, and for all the cells on the line;

(6) recording two positions, if they exist, along the line for which variations in signal level have passed from a value greater than the threshold value to a value lower than the inverse of the threshold value;

(7) verifying the distance between the two recorded positions, when they exist, is greater than a predetermined value, satisfaction of the conditions of steps (6) and (7) determining the presence of the compression device; and (8) carrying out of steps (e) to (h) in a zone delimited by the two positions recorded in step (6) and the minimum and maximum positions in depth established in step (2).

BRIEF DESCRIPTION OF THE DRAWINGS

The description refers to the accompanying figures, which represent respectively.

DETAILED DESCRIPTION OF THE INVENTION

Although the following description will be given relative to the examination of a breast, the method described may be applied to any other organ consisting of tissues of various natures having various coefficients of attenuation of X-rays.

In application of the method of the invention to mammography, the breast under examination, as is well known, is made up of adipose tissue and of glandular tissue (mammary gland).

In a radiographic examination, the region of the breast to be examined is that made up of glandular tissue and it is therefore of particular interest to be able to establish the parameters of exposure to X-rays of the breast most adapted to the region of interest, i.e., the glandular tissue.

After establishment of the parameters of pre-exposure from a table of automatic optimization of parameters, a given theoretical composition of the breast and an estimated radiologic thickness of the breast, and in order for the dose of X-rays to be low but sufficient to obtain a pre-exposure image of sufficient quality for differentiation of the glandular tissue of the breast tissue, there are established in a digital imagery X-ray device a minimum dose level and a maximum dose level of X-ray irradiation from a predetermined mechanical thickness of the breast that is converted into a minimum threshold signal level and a maximum threshold signal level, readable by a detector of the device.

As is known, the parameters of the beam include, among other things, the voltage applied to the X-ray tube (kV), the product of the anodic current multiplied by the duration of exposure (mAs), the focal track used, the filter and the positioning of the beam.

The given theoretical composition of the breast is an a priori composition for the breast, for example 50% of fibrous tissue and 50% of glandular tissue.

Having selected a given theoretical composition of the breast, an estimated radiologic thickness of the breast may be determined corresponding to the mechanical thickness of the breast multiplied by the coefficient of attenuation of X-rays for the theoretical composition of the breast; for example, with the above selection the estimated radiologic thickness would be 0.93×mechanical thickness.

To maintain a low exposure dose, the mAs is selected low, for example at a value of 1 to 4.

Figure 1:
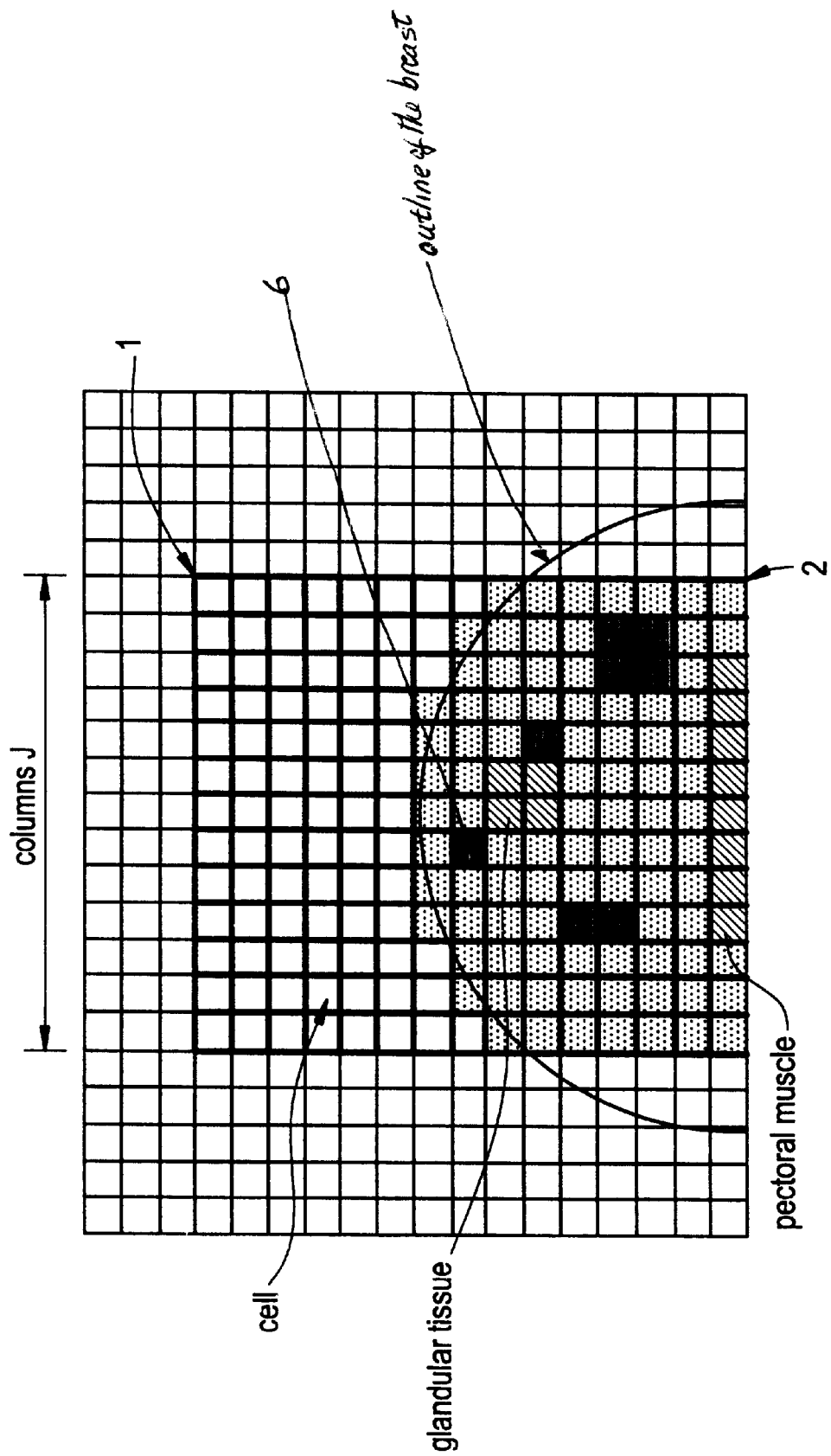
FIG. 1, a schematic representation of a multi-cellular image according to an embodiment the method.

After pre-exposure of the breast, as shown in FIG. 1, there is created in a zone of interest of the pre-exposure field a multi-cellular image 1 comprising columns j, each cell of which is indexed with respect to a reference point 2 that represents the chest wall. Each cell represents the logarithmic mean of the signal levels between the previously established minimum threshold level and the maximum threshold signal level of a predetermined number of pixels of the detector. Thus, for a rectangular multi-cellular image 16 cm×15 cm in size, cells of 1cm ×1 cm may be selected.

Then the position with respect to the reference point 2 of the cell in each column which presents the minimum signal level is determined for each column, in order thus to define a set of retained cells.

Then, the cell 6 most distant from the reference point 2 is selected from the set of retained cells. This prevents confusion with the pectoral muscle, which is near the chest wall.

Figure 2:
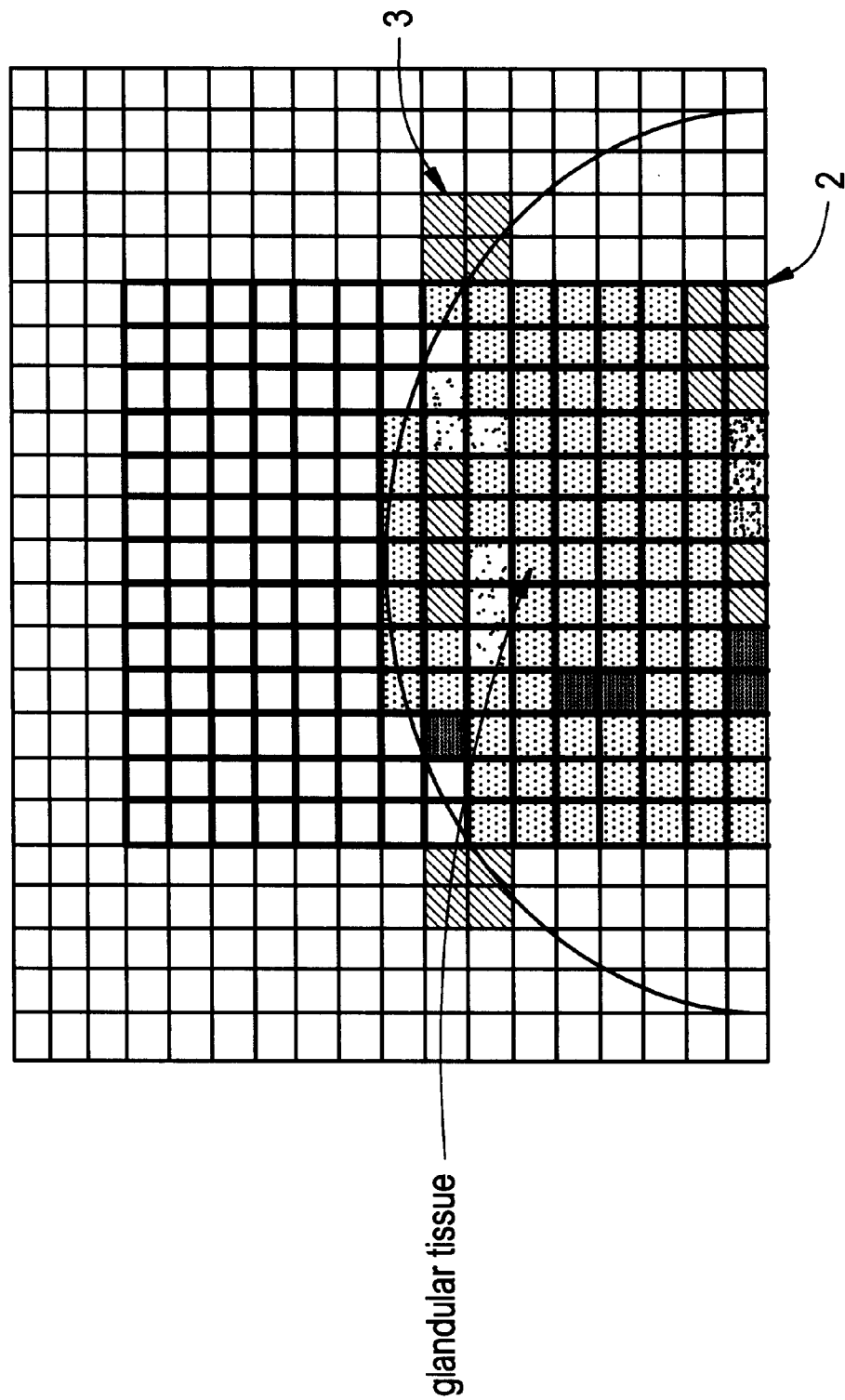
FIG. 2, a schematic representation of the zone of tissue of predetermined nature as established by the method.

As shown by FIG. 2, a band (or row) 3 parallel to the reference point 2, the width of which is proportional to the distance with respect to the reference point 2, is determined on either side of the retained cell 6, and the cell having the absolute minimum signal level is sought in this band. This absolute minimum signal level is used to establish the parameters of exposure for examination of the breast.

Figure 3:
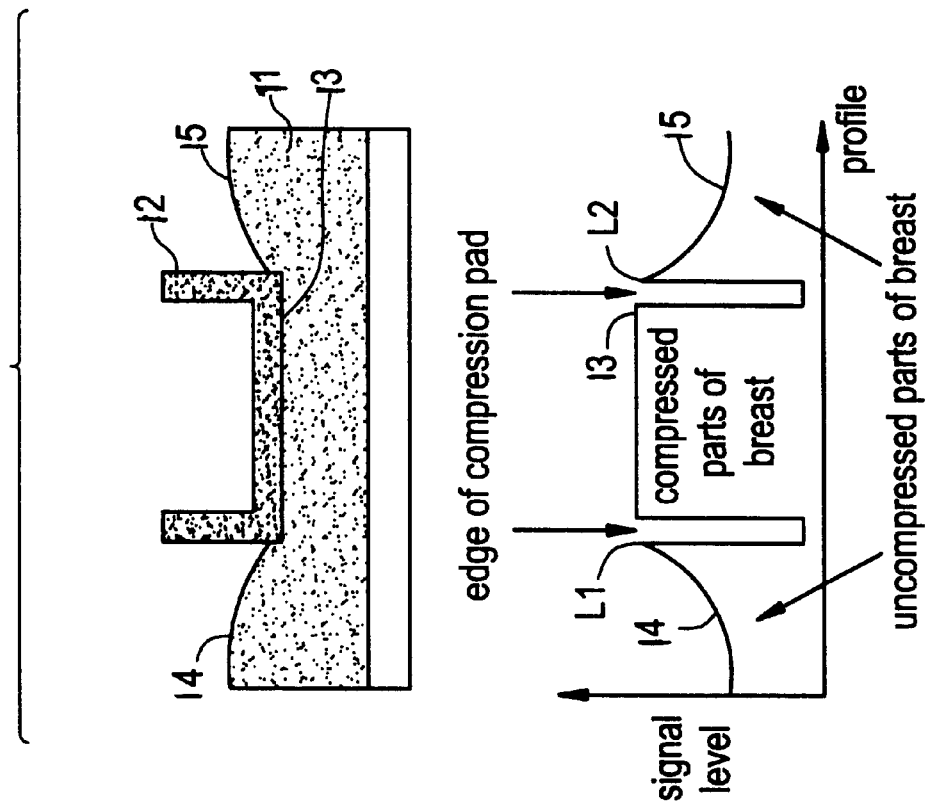
FIG. 3, a schematic representation showing the effect of use of a device for compression of the organ part examined relative to acquisition of the image of the organ part examined.

In the case of a radiologic examination of the breast 11, as shown in FIG. 3, the breast is compressed by means of a compression pad 12, which, as is known, has the general form of a rectangular frame, thus forming a compressed zone 13 of the breast constituting the zone of interest to be examined, and uncompressed zones 14 and 15.

In the method of automatic detection of glandular tissue of the breast, given by way of example, the presence of the pad must then be detected and its effects, as well as those due to uncompressed zones of the breast, eliminated. The edges of the compression pad attenuate the signal level to a much greater extent than the breast tissues, whether the latter are compressed or not. To suppress this effect, after determination in each column of the position of the cell of minimum signal level, a step of elimination of all the cells having a signal level below the minimum threshold signal level initially established is carried out.

On the other hand, the uncompressed zones 14, 15 of the breast 11 are thicker than the compressed zone 13 of the breast, and these uncompressed zones 14, 15 attenuate the X-ray beam more strongly and consequently the signal levels are weaker in these uncompressed zones 14, 15. The signal level curves correspond to the compressed and uncompressed areas of the breast as well as the compression pad edges as shown in FIG. 3. More precisely, referring to FIG. 3, the signal level increases in the uncompressed zones 14 and 15 up to the edges of the compression pad, where the level drops abruptly to rise again, equally abruptly, in the compressed zone 13. The effect described above is used to detect the presence of the compression pad 12 and to limit the field of the image to the compressed zone 13 of the breast. For that, after having eliminated all the cells not comprising a sufficient number of pixels of a value between the minimum threshold level and the maximum threshold level, the positions of minimal depth (Pmin) and of maximum depth (Pmax) of the pad with respect to the reference point are established (these positions generally being Pmin=3 cm and Pmax=4 cm) and a threshold value, for example corresponding to a threshold factor multiplied by the lowest minimum mean signal value determined for the cells, is established (the threshold factor generally being 3).

A line situated between the positions Pmin and Pmax is then established, and the variations in signal level between two consecutive cells along the line (derived from the signal level curve of FIG. 3), and for all the cells along the line, are compared to the threshold value. The two positions for which the variation in signal level passes from a value greater than the threshold to a value lower than the inverse of the threshold (−threshold value) are recorded. These two positions perhaps correspond to the positions of width L1 and L2 of the compression pad.

The operator then checks to see that the distance between the two recorded positions L1 and L2 is greater than a predetermined value (generally 4 cm) and, if the condition is satisfied, this means that a compression pad is present. The operator then proceeds as described above, but for the cells between the recorded positions L1, L2, Pmin and Pmax, to selection of the cell of minimum signal level having the position most distant from the reference point (chest wall), to determination of a band parallel to the reference point including the retained cell and of a width proportional to the distance of the latter with respect to the reference point, and to search in this band for the cell having the absolute minimum signal level. This signal level is then used to establish the parameters of exposure to X-rays. The width of the band preferably depends upon the position of the retained cell with regard to the reference point. In effect, a retained cell situated near the reference point is the indication of a breast of small volume and consequently the determined band will be narrow (to avoid including part of the pectoral muscle in it.) On the contrary, if the retained cell is situated far from the reference point, the breast is larger in volume and the band may be wider without risk of including the pectoral muscle in it.

Various modifications in structure and/or function and/or steps may be made by one skilled in the art to the disclosed embodiments without departing from the scope and extent of the invention.

What is claimed is:

1. A method for automatic detection of a tissue of predetermined nature in an organ part examined by digital X-ray radiography, comprising the steps of:

a) establishing parameters of pre-exposure from a table of automatic optimization of parameters, a given theoretical composition and an estimated radiologic thickness of the organ part examined and for a low but sufficient dose of X-rays to obtain a pre-exposure image of sufficient quality for the differentiation of tissues of the organ part examined;

b) establishing a minimum dose level and of a maximum dose level from a predetermined mechanical thickness of the organ part examined and conversion of these dose levels into a minimum threshold signal level and a maximum signal threshold level, readable by a detector;

c) pre-exposing the organ part examined to obtain a pre-exposure image;

d) creation in a zone of interest of the field of the pre-exposure image of a multi-cellular image of columns in which each cell indexed with regard to a reference point represents the logarithmic mean of the signal levels between the minimum threshold level and the maximum threshold level of a predetermined number of pixels of the detector;

e) determination in each column of the position, with respect to the reference point, of the cell having the minimum signal level to obtain a set of retained cells;

f) selection from the set of retained cells of the one whose position is most distant from the reference point;

g) determination of a band, parallel to the reference point, including the retained cell, the width of which is proportional to the distance of the cell selected with respect to the reference point and search in this band for the cell having the absolute minimum signal level; and h) using the absolute minimum signal level to establish the parameters of exposure of the organ part examined by X-rays.

2. The method according to claim 1, wherein after step (d) and before steps (e) to (h), the method additionally includes:

(1) elimination of all cells having a signal level below the minimum threshold signal level established in step (a);

(2) establishing the minimum position and a maximum position in depth, determined from the reference point, of a device which may perhaps be present for compression of the organ part examined;

(3) establishing a threshold value;

(4) establishing a line situated between the minimum and maximum positions in depth of any possible compression device and parallel to the reference point;

(5) comparing the threshold value of the variation in signal level between two consecutive cells along the line, and for all the cells on the line;

(6) recording two positions, if they exist, along the line for which variations in signal level have passed from a value greater than the threshold value to a value lower than the inverse of the threshold value;

(7) verifying the distance between the two recorded positions, when they exist, is greater than a predetermined value, satisfaction of the conditions of steps (6) and (7) determining the presence of the compression device; and (8) carrying out of steps (e) to (h) in a zone delimited by the two positions recorded in step (6) and the minimum and maximum positions in depth established in step (2).

3. The method according to claim 1, wherein the organ part examined is a breast.

4. The method according to claim 2, wherein the organ part examined is a breast.

5. The method according to claim 3, wherein the zone of interest consists of the glandular tissue of the breast.

6. The method according to claim 4, wherein the zone of interest consists of the glandular tissue of the breast.

7. The method according to claim 3, wherein the reference point consists of the chest wall.

8. The method according to claim 4, wherein the reference point consists of the chest wall.

* * * * *